US010137292B2

(12) United States Patent
Dabel

(10) Patent No.: US 10,137,292 B2
(45) Date of Patent: Nov. 27, 2018

(54) WATER RESISTANT CATHETER COVER

(71) Applicant: Pascal Dabel, Scott Depot, WV (US)

(72) Inventor: Pascal Dabel, Scott Depot, WV (US)

( * ) Notice: Subject to any disclaimer, the term of this patent is extended or adjusted under 35 U.S.C. 154(b) by 10 days.

(21) Appl. No.: 14/208,584

(22) Filed: Mar. 13, 2014

(65) Prior Publication Data

US 2015/0257833 A1 Sep. 17, 2015

(51) Int. Cl.
*A61M 25/02* (2006.01)
*A61B 46/20* (2016.01)
*A61B 46/10* (2016.01)
*A61M 25/00* (2006.01)
*A61M 39/16* (2006.01)
*A61M 1/36* (2006.01)
*A61M 39/20* (2006.01)

(52) U.S. Cl.
CPC ........... *A61M 39/165* (2013.01); *A61B 46/10* (2016.02); *A61M 1/3661* (2014.02); *A61M 25/00* (2013.01); *A61M 39/20* (2013.01); *A61B 2046/205* (2016.02); *A61M 25/02* (2013.01)

(58) Field of Classification Search
CPC .......... A61M 25/02; A61M 2025/0273; A61M 2025/0266; A61M 2025/0253; A61M 2025/0246
See application file for complete search history.

(56) References Cited

U.S. PATENT DOCUMENTS

| | | | | |
|---|---|---|---|---|
| 4,397,641 A * | 8/1983 | Jacobs | ..................... | 604/180 |
| 6,124,521 A * | 9/2000 | Roberts | ................ | A61M 25/02 |
| | | | | 602/42 |
| 8,319,003 B2 * | 11/2012 | Olsen | ..................... | A61F 5/443 |
| | | | | 602/46 |
| 2002/0051861 A1 * | 5/2002 | Jennings | ................ | B65D 27/30 |
| | | | | 428/67 |
| 2002/0169405 A1 * | 11/2002 | Roberts | ................ | A61F 13/023 |
| | | | | 602/43 |
| 2007/0088281 A1 * | 4/2007 | Ritchey | ................ | A61F 15/004 |
| | | | | 604/174 |
| 2008/0208145 A1 * | 8/2008 | McCulloch | .................. | 604/263 |
| 2012/0143160 A1 * | 6/2012 | Song | ............................. | 604/361 |
| 2014/0121649 A1 * | 5/2014 | Calco | .................. | A61F 13/0206 |
| | | | | 604/543 |

* cited by examiner

*Primary Examiner* — Matthew F Desanto
(74) *Attorney, Agent, or Firm* — Dunlap Bennett & Ludwig PLLC

(57) ABSTRACT

A catheter covering device with at least a sleeve and an adhesive film is provided. The catheter covering device may further include a water indicator attached to the adhesive film and a desiccant paper attached to the water indicator. The adhesive film may include a larger diameter than the water indicator and the desiccant paper. Thereby the adhesive film is exposed around the circumference of the water indicator and desiccant paper. A catheter may be inserted into the sleeve and the adhesive film may be adhered to a user's skin. The catheter covering device may thereby protect the catheter from the elements. If moisture enters the catheter covering device, the desiccant paper may absorb the moisture and activate the water indicator, indicating to the user that the catheter covering device has been contaminated.

6 Claims, 3 Drawing Sheets

WATER RESISTANT CATHETER COVER

CROSS-REFERENCE TO RELATED APPLICATION

This application claims the benefit of priority of U.S. provisional application No. 61/772,417, filed Mar. 4, 2013, the contents of which are herein incorporated by reference.

BACKGROUND OF THE INVENTION

The present invention relates to a catheter cover and, more particularly, to a catheter cover that may protect the catheter from water.

Dialysis patients that have to use catheters are not allowed to shower or swim for weeks and up to months at a time. The patients thereby become dirty, uncomfortable, and are more prone to infection. The only way a patient may clean themselves is by using a washcloth or sponge which promotes cross contamination of the catheter site. Further, the patients are at increased risk for blood stream infections since there are no appropriate methods of protecting the catheter site.

Currently, to cover the catheter, gauze bases may be used. However, the gauze bases only protect the entry site into the skin and are not water resistant. The gauze does not prevent contaminants from making contact with the catheter or entry site into the skin. The gauze and tape absorbs moisture, dead skin cells, and bacteria. All of the above promote infection instead of preventing it. Further, the gauze and tape fall off easily leaving little to no protection.

As can be seen, there is a need for a cover that protects the catheter from the elements and allows for an improvement in quality of life due to increased hygiene.

SUMMARY OF THE INVENTION

In one aspect of the present invention, a catheter covering device comprises: a water resistant sleeve comprising a first end and a second end, wherein the first end comprises a rim forming an opening into the sleeve; an adhesive film attached to the rim of the water resistant sleeve, wherein the adhesive film comprises an opening leading into the sleeve.

In another aspect of the present invention, a method of covering a catheter attached to a body comprises: providing a water resistant sleeve comprising a first end a first end and a second end, wherein the first end comprises a rim forming an opening into the sleeve; sterilizing/decontaminating an area of the body surrounding the catheter; placing the catheter through the opening and within the sleeve; and adhering the rim of the water resistant sleeve to the body.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes a plastic covering shield for hemodialysis catheters to prevent infections and water exposure. The present invention covers the entire hemodialysis catheter and entry site into the skin, therefore allowing patients to freely shower and swim since the present invention is water resistant and impermeable. The closed circuit environment of the present invention also limits contamination and bacterial exposure to the catheter/skin entry site, and therefore reduces the number of infections. The present invention may not contain gauze and may include polyurethane sleeve which allows patients to shower and swim due to the water resistant properties. The entire catheter unit and skin entry site is protected which decreases pathogen exposure.

The polyurethane sleeve has a high moisture/water vapor transmission rate which will prevent accumulation of moisture (sweat and condensation) inside of the closed circuit environment once applied to the skin. Water cannot get into the device but moisture freely passes out at a rate higher than that of sweat produced from the area of skin being protected.

Broadly, an embodiment of the present invention provides a catheter covering device with at least a sleeve and an adhesive film. The catheter covering device may further include a water indicator attached to the adhesive film and a desiccant paper attached to the water indicator. The adhesive film may include a larger diameter than the water indicator and the desiccant paper. Thereby the adhesive film is exposed around the circumference of the water indicator and desiccant paper. A catheter may be inserted into the sleeve and the adhesive film may be adhered to a user's skin. The catheter covering device may thereby protect the catheter from the elements. If moisture enters the catheter covering device, the desiccant paper may absorb the moisture and activate the water indicator, indicating to the user that the catheter covering device has been contaminated. The white to red color change is visible through the device.

Figure 1:
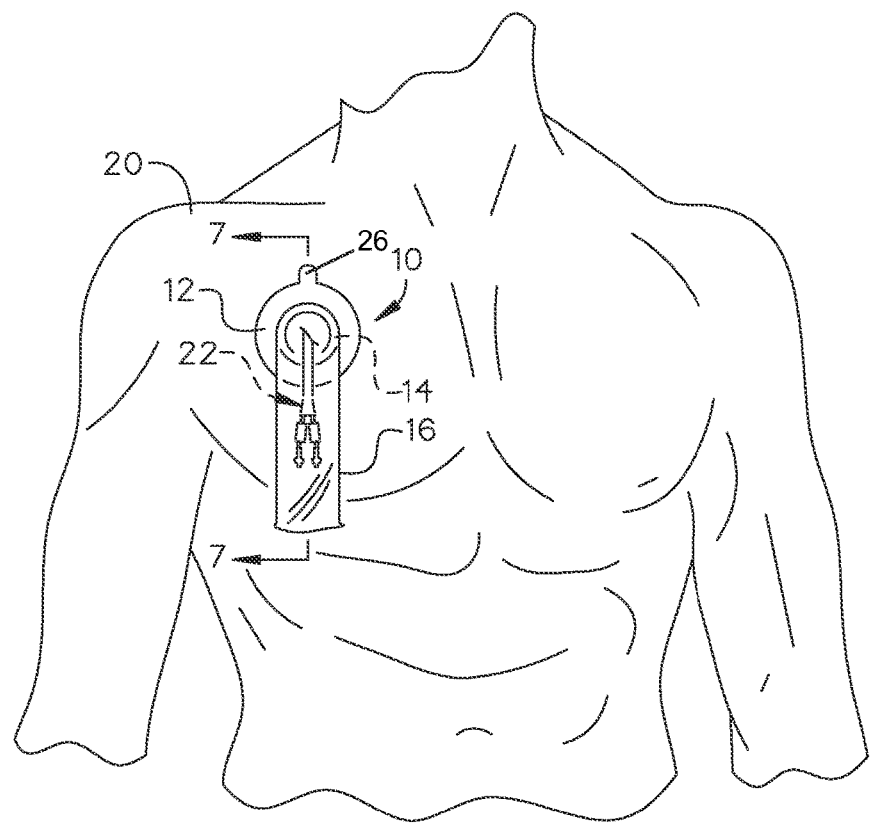
FIG. 1 is a front view of the present invention shown in use.
Figure 2:
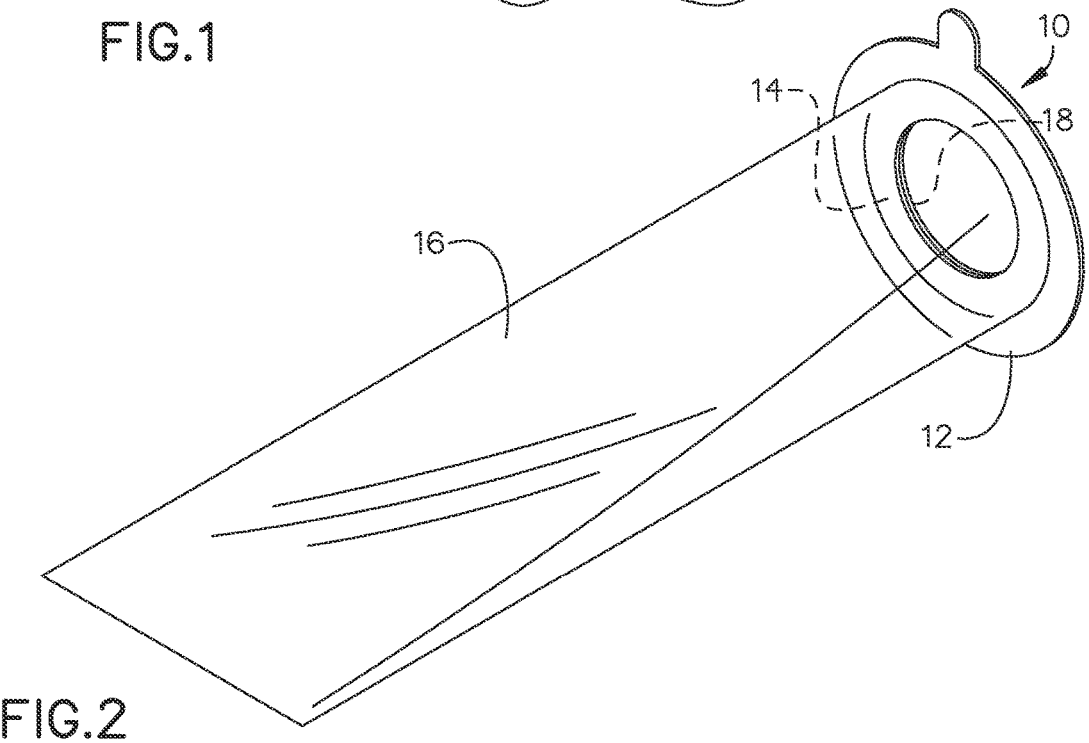
FIG. 2 is a perspective view of the present invention.
Figure 3:
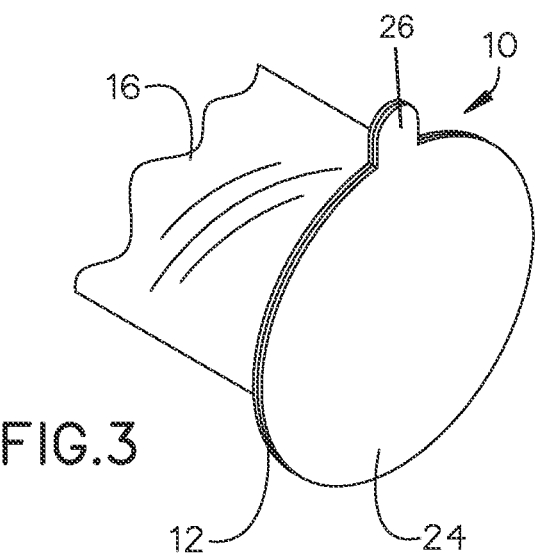
FIG. 3 is a rear detail perspective view of the present invention shown with a wax paper.
Figure 4:
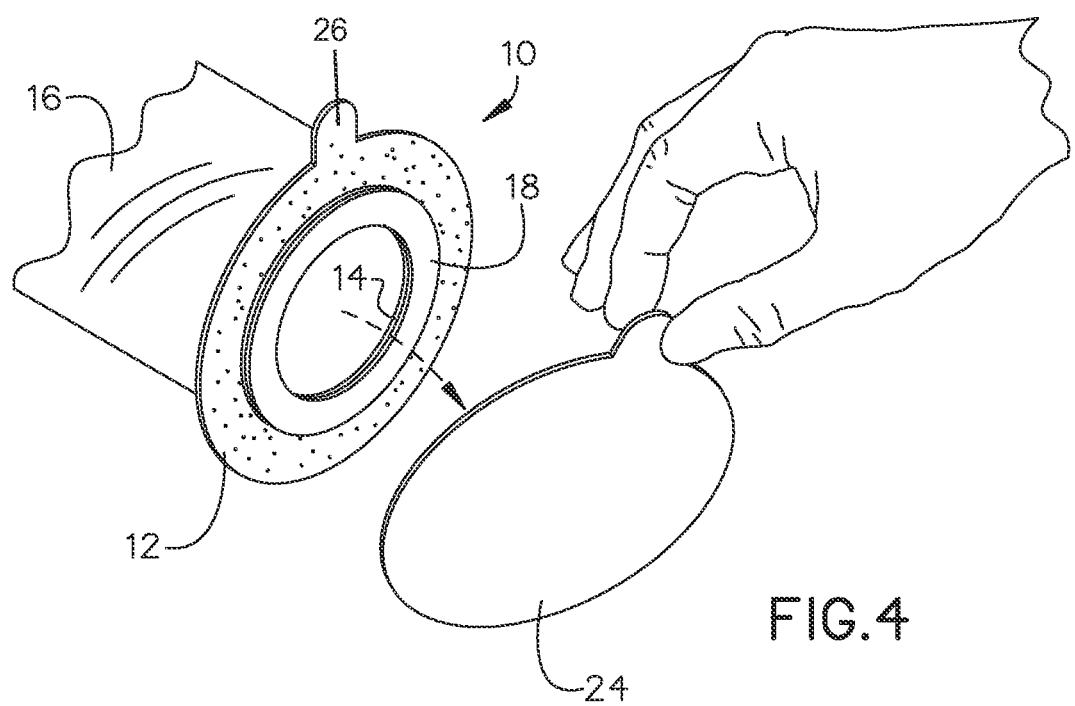
FIG. 4 is a rear detail perspective view of the present invention demonstrating the removal of the wax paper of FIG. 3.
Figure 5:
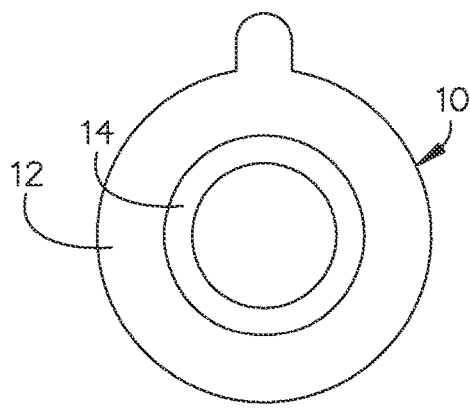
FIG. 5 is a front view of the present invention shown with a dry water indicator.
Figure 6:
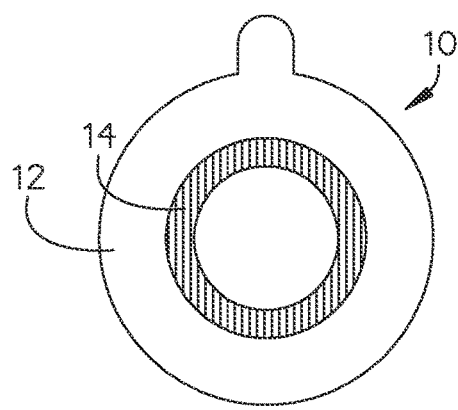
FIG. 6 is a front view of the present invention shown with a wet water indicator.
Figure 7:
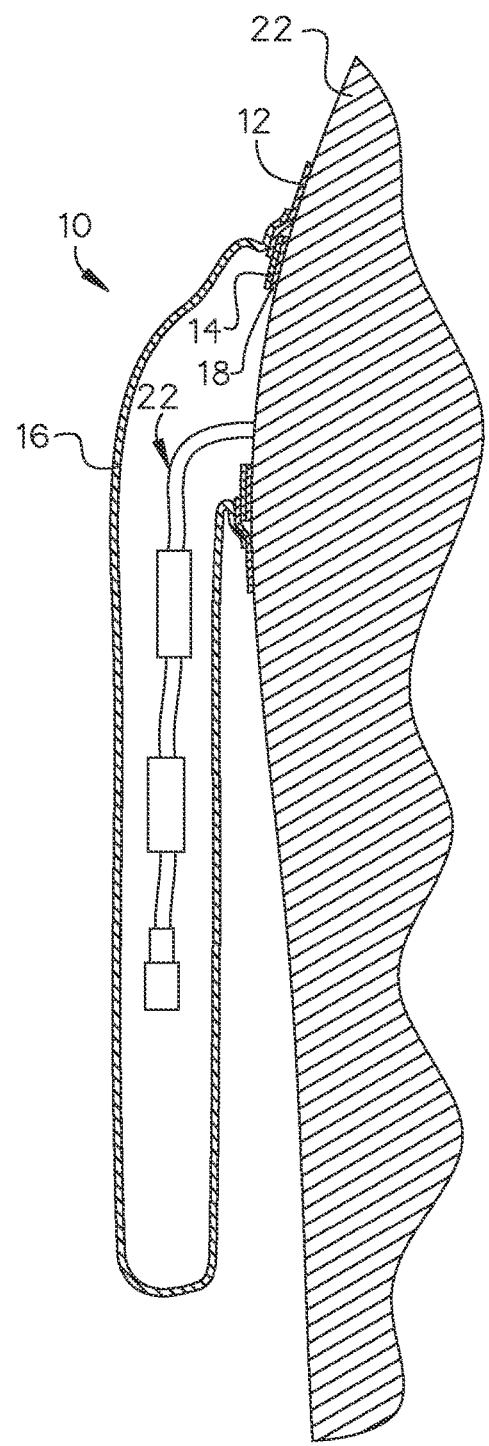
FIG. 7 is a section detail view of the present invention along line 7-7 of FIG. 1.

Referring to FIGS. 1 through 7, the present invention may include a catheter covering device 10. The catheter covering device 10 may include a water resistant sleeve 16. The water resistant sleeve 16 may include a first end and a second end. The first end may include a rim forming an opening into the sleeve 16. The second end may be a closed end. The water resistant sleeve 16 may be made of a polymer, such as a plastic. For example, the water resistant sleeve 16 may be made of an Ultra Violet protective polyethylene. In certain embodiments, the water resistant sleeve 16 may be approximately seven and a half inches long with about a one inch diameter. The sleeve 16 may be formed to fit over the catheter 22 of a user 20.

The present invention further includes an adhesive film 12. The adhesive film 12 is attached to the rim of the water resistant sleeve 16. The adhesive film 12 includes an opening that leads into the sleeve 16. In certain embodiments, the adhesive film 12 includes a first side and a second side. The rim of the sleeve 16 may be sealed, such as radiofrequency welded, to the first side of the adhesive film 12. The second side of the adhesive film 12 may include the adhesive material. The adhesive film 12 and the water resistant sleeve 16 may prevent water from contacting the catheter 22 and the skin surrounding the catheter 22. In certain embodiments, the adhesive film 12 is a waterproof tape, such as 3M Tegaderm®. The adhesive film 12 may have a round shape, however the waterproof tape 12 may be any shape desired.

In certain embodiments, the present invention may include a water indicator 14. The water indicator 14 may be attached to the adhesive film 12. The water indicator 14 may be attached circumferentially around the opening of the adhesive film 12. In certain embodiments, the water indicator 14 may change color, from white to red, when moisture comes into contact with the water indicator 14. This indicates to the user 20 that moisture has entered the barrier and the user 20 may exit the water and remove the sleeve 16 and replace with a new device. The water indicator 14 may include 3M 5557® water indicator tape, an indigo color indicating paper, an electronic tape detector or the like.

The present invention may further include a desiccant paper 18. The desiccant paper 18 may be attached to the water indicator 14. In certain embodiments, the desiccant paper 18 may include an opening aligning with the opening of the adhesive film 12 and the water indicator 14. In certain embodiments of the present invention, the water indicator 14 may be attached to the first side of the adhesive film 12 and the desiccant paper 18 may be attached to the opposite side of the water indicator 14. Therefore, the water indicator 14 may be sandwiched in between the adhesive film 12 and the desiccant paper 18. The desiccant paper 18 may absorb moisture and transmits the moisture to the water indicator 14, which may change color when exposed to water.

In certain embodiments, the present invention may further include additional components. For example, the present invention may include a paper cover 24 and a tab 26. The paper cover 24 may be a wax paper that covers the adhesive when the present invention is not being used. The tab 26 may extend from the parameter of the adhesive film 12 and from the wax paper 24. The tab 26 may or may not include an adhesive material. Therefore, when the user 20 has the catheter covering device 10 attached to the skin, the user 20 may pull the tab 26 in order to remove the catheter covering device.

A method of using the present invention may include the following. First a user may provide the catheter covering device mentioned above. The user may groom an area of the body surrounding the catheter, which may include shaving and/or cleaning the area. The user may place the catheter through the opening and within the sleeve. The air may be squeezed out of the plastic sleeve. The rim of the water resistance sleeve may be adhered to the body by using waterproof tape around the catheter insertion site into the skin. The waterproof tape may be pressed firmly against dry and hairless skin around the catheter. This may prevent water from getting into the device or making contact with the catheter in the shower or pool. If water were to accidentally get through the waterproof tape, the water may come into contact with the water indicator which may cause a color change, for example from white to red, blue to white or the like. The patient may then know to get out of the shower or pool and dry themselves off thoroughly. The device may then be removed from the skin by pulling on the tab and discarded.

A method of making the present invention may include the following. Medical grade skin tape may be cut into circular shape. The color changing/water indicating tape may be cut with desiccant paper into a smaller circular shape, i.e. a smaller diameter. The present invention may be layered so that the water indicator is between the adhesive film and the desiccant paper. An opening may be cut into the middle or the circle making a ring. These components may be glued or taped together. Polyurethane plastic may then be shaped into a sleeve. The opening of the of the sleeve may be a similar size of the hole cut into the combined components above. The sleeve may be radiofrequency welded onto the non tape/skin side of the above unit. The entire device may need to be created in a sterile environment.

It should be understood, of course, that the foregoing relates to exemplary embodiments of the invention and that modifications may be made without departing from the spirit and scope of the invention as set forth in the following claims.

What is claimed is:

1. A catheter covering device comprising:
   a sleeve formed of a water resistant and breathable polymer and comprising a first end and a second end, wherein the first end comprises a rim forming an opening into the sleeve;
   an adhesive film comprising a first side and a second side, wherein the first side is attached to the rim of the sleeve and the second side comprises an adhesive, wherein the adhesive film comprises an inner edge forming an opening leading into the sleeve;
   a water indicator comprising a ring shape having a first side, a second side, an inner edge and an outer edge, wherein the first side of the water indicator is attached to the second side of the adhesive film, wherein an opening formed by the inner edge aligns with the opening of the adhesive film and leads into the sleeve, wherein an outer edge of the adhesive film extends beyond the outer edge of the water indicator so that the adhesive is exposed; and
   a desiccant paper attached to the water indicator, wherein the water indicator is sandwiched in between the adhesive film and the desiccant paper.

2. The catheter covering device of claim 1, wherein the water indicator changes color when the water indicator is wet.

3. The catheter covering device of claim 1, further comprising a tab extending from the perimeter of the adhesive film.

4. The catheter covering device of claim 1, wherein the polymer is polyurethane.

5. A catheter covering device comprising:
   a sleeve formed of a water resistant and breathable polymer comprising a first end and a second end, wherein the first end comprises a rim forming an opening into the sleeve;
   an adhesive film comprising a first side and a second side, wherein the first side is attached to the rim of the sleeve and the second side comprises an adhesive, wherein the adhesive film comprises an inner edge forming an opening leading into the sleeve;
   a water indicator comprising a ring shape having a first side, a second side, an inner edge and an outer edge, wherein the first side of the water indicator is attached to the second side of the adhesive film, wherein an opening formed by the inner edge aligns with the opening of the adhesive film and leads into the sleeve;

a desiccant paper comprising a ring shape having a first side, a second side, an inner edge and an outer edge, wherein the first side of the desiccant paper is attached to the second side of the water indicator, wherein an opening formed by the inner edge of the disaccant paper aligns with the opening of the adhesive film and the water indicator and leads into the sleeve, wherein an outer edge of the adhesive film extends beyond the outer edge of the water indicator and an outer edge of the desiccant paper so that the adhesive is exposed.

6. The catheter covering device of claim 5, wherein the polymer is polyurethane.

* * * * *